(12) United States Patent  
Miyano et al.

(10) Patent No.: US 9,381,070 B2
(45) Date of Patent: Jul. 5, 2016

(54) DENTAL MIXER

(71) Applicant: GC CORPORATION, Bunkyo-ku (JP)

(72) Inventors: Tatsunosuke Miyano, Itabashi-ku (JP); Kazuma Noguchi, Soka (JP)

(73) Assignee: GC CORPORATION, Bunkyo-ku (JP)

( * ) Notice: Subject to any disclaimer, the term of this patent is extended or adjusted under 35 U.S.C. 154(b) by 98 days.

(21) Appl. No.: 14/191,865

(22) Filed: Feb. 27, 2014

(65) Prior Publication Data

US 2014/0246457 A1    Sep. 4, 2014

(30) Foreign Application Priority Data

Mar. 1, 2013    (JP) .................................. 2013-040448

(51) Int. Cl.
| | |
|---|---|
| *B67D 7/70* | (2010.01) |
| *A61C 5/06* | (2006.01) |
| *B05C 17/005* | (2006.01) |

(52) U.S. Cl.
CPC ................. *A61C 5/068* (2013.01); *A61C 5/064* (2013.01); *B05C 17/00553* (2013.01); *B05C 17/00593* (2013.01)

(58) Field of Classification Search
CPC ................... B05C 17/00506; B05C 17/00593; F16L 37/133; A61M 2005/1787; A61M 5/19; A61M 5/2448; A61M 5/3294
USPC ....................... 222/145.1, 145.5, 153.14, 137; 220/319, 320, 321, 326; 285/315–316; 239/600; 604/191
See application file for complete search history.

(56) References Cited

U.S. PATENT DOCUMENTS

| | | | | |
|---|---|---|---|---|
| 2,784,987 | A | * | 3/1957 | Corcoran ........................ 285/82 |
| 3,604,410 | A | * | 9/1971 | Whitacre ............. A61B 5/1427 600/575 |
| 4,367,737 | A | * | 1/1983 | Kozam .................... A61M 5/19 604/191 |
| 4,717,077 | A | * | 1/1988 | Takata .................. B05B 15/069 239/548 |
| 4,871,090 | A | * | 10/1989 | Hoffmann ........................ 222/81 |
| 4,974,756 | A | * | 12/1990 | Pearson et al. ................ 222/562 |
| 4,981,241 | A | * | 1/1991 | Keller ............................ 222/137 |
| 5,228,599 | A | | 7/1993 | Keller |
| 5,240,146 | A | * | 8/1993 | Smedley ................. A61M 5/19 222/137 |

(Continued)

FOREIGN PATENT DOCUMENTS

| | | |
|---|---|---|
| EP | 0 723 807 A2 | 7/1996 |
| EP | 0 723 807 A3 | 7/1996 |

(Continued)

*Primary Examiner* — Patrick M Buechner
*Assistant Examiner* — Randall Gruby
(74) *Attorney, Agent, or Firm* — Oblon, McClelland, Maier & Neustadt, L.L.P.

(57) ABSTRACT

To provide a dental mixer capable of easily, certainly locking a mixing tip to a syringe body, easily removing the mixing tip, and thereby having easy handling property. The dental mixer includes a syringe body 1 and a sleeve 3. The mixing tip 2 includes a housing 2*a*, a paste guiding member 2*b* and a plate spring-shaped locking members 2*c* and 2*c*. The plate spring-shaped locking members 2*c* and 2*c* have pawl portions 2*ca* and 2*ca* on the tip-end side thereof, and the pawl portions 2*ca* and 2*ca* are locked, by elasticity, with locking grooves 1*c* and 1*c* between the syringes 1*a* and 1*a*. The sleeve 3 has a shape to cover at least the pawl portions 2*ca* and 2*ca* when sliding toward the outlet side of the housing 2*a*, and thereby to prevent the locking of the pawl portions 2*ca* and 2*ca* by elasticity from canceling.

2 Claims, 4 Drawing Sheets

(56) References Cited

U.S. PATENT DOCUMENTS

| | | | | |
|---|---|---|---|---|
| 5,301,842 A * | 4/1994 | Ritter | B65D 81/325 | 220/617 |
| 5,314,412 A * | 5/1994 | Rex | A61M 5/19 | 222/137 |
| 5,354,284 A * | 10/1994 | Haber | A61M 5/19 | 630/191 |
| 5,383,906 A * | 1/1995 | Burchett | A61J 7/0046 | 222/133 |
| 5,445,614 A * | 8/1995 | Haber | A61M 5/19 | 604/191 |
| 5,462,204 A * | 10/1995 | Finn | | 222/137 |
| 5,562,219 A * | 10/1996 | de Pous | B65D 83/48 | 215/274 |
| 5,810,792 A * | 9/1998 | Fangrow et al. | | 604/533 |
| 5,824,012 A * | 10/1998 | Burchett | A61J 7/0046 | 215/11.1 |
| 6,030,214 A * | 2/2000 | Zwingenberger | A61C 5/064 | 433/80 |
| 6,048,201 A * | 4/2000 | Zwingenberger | | 433/90 |
| 6,135,631 A * | 10/2000 | Keller | | 366/339 |
| 6,527,203 B2 | 3/2003 | Hurray et al. | | 239/413 |
| 6,619,495 B1* | 9/2003 | Pares Montaner | B05B 11/3049 | 215/272 |
| 6,834,778 B2* | 12/2004 | Jinbo et al. | | 222/135 |
| 6,843,652 B2* | 1/2005 | Xie | A61C 5/064 | 433/48 |
| 6,964,434 B2* | 11/2005 | Beck et al. | | 285/7 |
| 6,976,640 B2* | 12/2005 | Chen | B05B 1/005 | 239/290 |
| 7,556,618 B2* | 7/2009 | Sogaro | | 604/191 |
| 7,575,131 B2* | 8/2009 | Feinberg | A61B 17/00491 | 222/1 |
| 7,717,357 B2* | 5/2010 | Gantenbein | B01F 5/0619 | 222/145.6 |
| 8,033,429 B2* | 10/2011 | Keller | B05C 17/00506 | 222/137 |
| D688,952 S * | 9/2013 | Pappalardo | | D9/724 |
| 8,544,690 B2* | 10/2013 | Garcia | B05B 11/0013 | 222/147 |
| 8,550,311 B2* | 10/2013 | Cornet | B05B 11/3049 | 222/153.1 |
| 8,590,749 B2* | 11/2013 | Beranger | B05B 11/3049 | 222/153.09 |
| 8,820,552 B2* | 9/2014 | Pleyer | B05B 11/3049 | 215/272 |
| 8,919,609 B2* | 12/2014 | Wang | A61C 5/064 | 222/137 |
| 8,978,930 B2* | 3/2015 | Bublewitz et al. | | 222/145.6 |
| D726,551 S * | 4/2015 | Pappalardo | | D9/724 |
| 9,010,578 B2* | 4/2015 | Keller | B01F 5/0615 | 222/137 |
| 9,168,108 B2* | 10/2015 | Bublewitz | A61C 5/062 | |
| 2004/0150223 A1* | 8/2004 | Campau | | 285/308 |
| 2005/0035153 A1* | 2/2005 | Brown | B01F 5/0682 | 222/145.6 |
| 2005/0230422 A1* | 10/2005 | Muller et al. | | 222/145.6 |
| 2006/0071019 A1* | 4/2006 | Engelbrecht | A61C 5/064 | 222/94 |
| 2006/0157503 A1* | 7/2006 | Bublewitz | A61C 5/064 | 222/94 |
| 2006/0157508 A1* | 7/2006 | Suchan et al. | | 222/153.01 |
| 2006/0273115 A1* | 12/2006 | De Pous | B05B 11/0008 | 222/321.9 |
| 2008/0029542 A1* | 2/2008 | Keller | | 222/145.5 |
| 2008/0056065 A1* | 3/2008 | Keller | | 366/339 |
| 2008/0083782 A1* | 4/2008 | Heusser et al. | | 222/145.5 |
| 2008/0232187 A1 | 9/2008 | Miyano et al. | | |
| 2008/0287880 A1* | 11/2008 | Keller | | 604/191 |
| 2010/0012210 A1* | 1/2010 | Miyano et al. | | 137/896 |
| 2010/0200614 A1* | 8/2010 | Von Rotz et al. | | 222/145.5 |
| 2011/0121035 A1* | 5/2011 | Greter et al. | | 222/145.1 |
| 2011/0319930 A1* | 12/2011 | Roush | A61B 17/00491 | 606/213 |
| 2012/0228329 A1* | 9/2012 | Staub | | 222/137 |
| 2014/0117044 A1* | 5/2014 | Pappalardo | | 222/137 |
| 2015/0291339 A1* | 10/2015 | Leue | B05C 17/00506 | 222/136 |

FOREIGN PATENT DOCUMENTS

| | | |
|---|---|---|
| EP | 1 389 448 A1 | 2/2004 |
| JP | 04-239477 A | 8/1992 |
| JP | 08-276125 A | 10/1996 |
| JP | 2008-229553 A | 10/2008 |
| WO | WO 2004/009249 A1 | 1/2004 |

* cited by examiner

FIG. 3
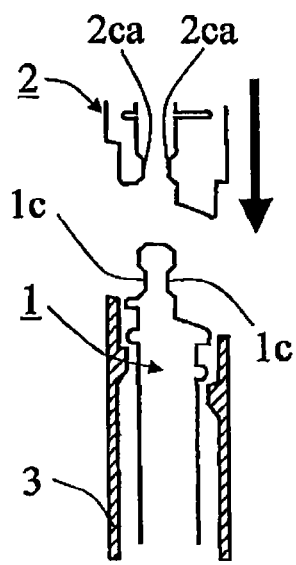
(I)
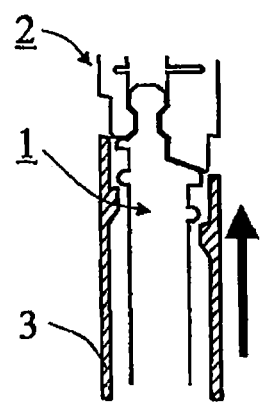
(II)
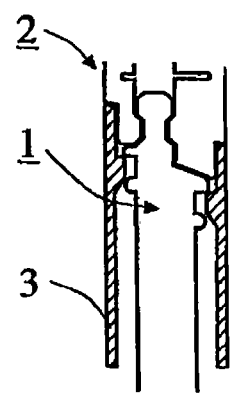
(III)

DENTAL MIXER

BACKGROUND OF THE INVENTION

1. Field of the Invention

The present invention relates to a dental mixer that is capable of easily and certainly locking a mixing tip to a syringe body which is fixed on a holder. The mixing tip is to mix and discharge a dental paste, and the syringe body includes parallel two syringes.

2. Description of the Conventional Art

When plural pastes are mixed, a static mixing tip has been generally used to mix pastes each extruded from a syringe housing the each paste, and the mixing tip is locked to a tip-end of a syringe body including plural syringes which are fixed in parallel.

The mixing tip is required to be easily locked to the syringe body. For example, Japanese Patent Laid-Open Application No. H08-276125 discloses such a mixing tip. In the technique, the mixing tip (a mixer) has an insertion projection provided on an lower end outer surface of the mixing tip, and a syringe body (a cartridge) has a projected piece to receive the insertion projection of the mixing tip. The mixing tip and the syringe body abut so that the projection insertion of the mixing tip intersects the projected piece of the syringe body, and the mixing tip is rotated by approximately 90° so that the projection insertion and the projected piece are locked. However, the mixing tip is not always certainly locked because the mixing tip is only rotated. Therefore, the mixing tip needs some mechanism to prevent from removing.

Further, for example Japanese Patent Application Laid-Open No. H04-239477 discloses a cartridge capable of locking a mixing tip more certainly. The technique uses plural syringes each having one male screw on each tip-end portion in a state of being disposed. In a state that the mixing tip abut against the tip-end portions of the syringes having the male screws, a coupling nut is screwed so as to cover the abutted syringes and mixing tip, and the mixing tip and syringes are connected. However, in the cartridge, the nut (coupling nut) needs to be screwed to the male screw part. Therefore, it takes time and effort to mount the mixing tip. Furthermore, a peculiar processing is necessary for forming the male screw in a state of disposing plural syringes.

As a similar mixing tip capable of being locked certainly, for example, Japanese Patent Application Laid-Open No. 2008-229553 discloses a mixing tip which is locked at two portions on a tip-end of a syringe body (a syringe holder) including two parallel syringes. The mixing tip includes a housing, a paste guiding member, and two locking members. The housing has a mixing element mounted inside thereof. The paste guiding member has paste inlets attached to nozzles of the two syringes, and a flow path portion for guiding pastes each extruded from each syringe into the housing from the pastes inlets. The paste guiding member is fixed on an end portion positioned on the side opposite to an outlet of the housing. The two locking members are fixed on or integrally with the pastes guiding member or the housing, and are for locking the mixing tip to the syringe body (the syringe holder). The two locking members each is a pawl portion to be locked with a locking hole formed on the syringe body (the syringe holder), and a projection to be inserted into a hole portion bored on the syringe body (the syringe holder). Or, the two locking members each is a pawl portion to be locked with the locking hole formed on the syringe body (the syringe holder).

Since the mixing tip is fixed only with the pawl portion to be locked with the locking hole of the syringe body (the syringe holder), the mixing tip needs to be locked strongly with the pawl portion. As a result, there is a problem that it takes time and effort when removing the strongly locked pawl portion.

SUMMARY OF THE INVENTION

The present invention is to solve the aforementioned problems, and an objective of the present invention is to provide a dental mixer capable of easily, certainly locking a mixing tip to a syringe body, easily removing the mixing tip, and thereby having easy handling property.

Means for Solving the Problem

The present inventors carried out earnest works to solve the aforementioned problems and, as a result, they found the following to complete the present invention. That is, a dental mixer includes a syringe body having two parallel syringes fixed on a holder, a mixing tip for mixing and discharging a dental paste in each syringe, and a sleeve slidably and externally fitted to the syringe. Since the dental mixer has a simple constitution, the dental mixer is easy in handing and excellent in productivity. Further, the mixing tip includes a housing, a paste guiding member, and a pair of plate spring-shaped locking members. The housing has a mixing element mounted inside thereof. The paste guiding member is provided at an end portion positioned on the side opposite to an outlet of the housing, and is for guiding a dental paste from the inside of the each syringe to the inside of the housing. The pair of plate spring-shaped locking members is constituted integrally with the paste guiding member or the housing, and each of the locking members has a pawl portion on the tip-end side thereof. The pawl portion of the each locking member is locked, by elasticity, with a pair of locking grooves each formed between the two syringes of the syringe body. The sleeve has a shape, which covers at least the pawl portion of each locking member when sliding toward the outlet side of the housing and thereby prevents the locking of the pawl portion by elasticity from canceling. In the above-mentioned constitution, the mixing tip is locked with the syringe body by using the two pawl portions and the sleeve holding the pawl portions. Therefore, it is not necessary to strongly lock the mixing tip only with the pawl portion, and the mixing tip is lightly locked by the pawl portion. As a result, attaching and detaching of the mixing tip are easy, and its handing is easy.

Namely, the present invention relates to a dental mixer including a syringe body having two parallel syringes fixed on a holder, a mixing tip for mixing and discharging a dental paste in each syringe, and a sleeve slidably and externally fitted to the syringe. The mixing tip includes a housing, a paste guiding member, and a pair of plate spring-shaped locking members. The housing has a mixing element mounted inside thereof. The paste guiding member is provided at an end portion positioned on the side opposite to an outlet of the housing, and is for guiding a dental paste from the inside of the each syringe to the inside of the housing. The pair of plate spring-shaped locking members is constituted integrally with the paste guiding member or the housing, and each of the locking members has a pawl portion on the tip-end side thereof. The pawl portion of the each locking member is locked, by elasticity, with a pair of locking grooves each formed between the two syringes of the syringe body. Further, the sleeve has a shape, which covers at least the pawl portion of each locking member when sliding toward the outlet side of the housing and thereby prevents the locking of the pawl portion by elasticity from canceling.

Effect of the Invention

The present invention relates to a dental mixer including a syringe body having two parallel syringes fixed on a holder, a mixing tip for mixing and discharging a dental paste in each syringe, and a sleeve slidably and externally fitted to the syringe. The mixing tip includes a housing, a paste guiding member, and a pair of plate spring-shaped locking members. The housing has a mixing element mounted inside thereof. The paste guiding member is provided at an end portion positioned on the side opposite to an outlet of the housing, and is for guiding a dental paste from the inside of the each syringe to the inside of the housing. The pair of plate spring-shaped locking members is constituted integrally with the paste guiding member or the housing, and each of the locking members has a pawl portion on the tip-end side thereof. The pawl portion of the each locking member is locked, by elasticity, with a pair of locking grooves each formed between the two syringes of the syringe body. Further, the sleeve has a shape, which covers at least the pawl portion of the each locking member when sliding toward the outlet side of the housing and thereby prevents the locking of the pawl portion by elasticity from canceling. Therefore, the dental mixer has a very simple constitution, is easy in handling, and is excellent in productivity. Further, the mixing tip is locked with the syringe body by using the two pawl portions and the sleeve holding the pawl portions. Therefore, it is not necessary to strongly lock the mixing tip only with the pawl portion, and the mixing tip is lightly locked by the pawl portion. As a result, attaching and detaching of the mixing tip are easy, and its handing is easy.

BRIEF EXPLANATION OF DRAWINGS

FIG. 3 is a brief explanation view illustrating a state of locking a mixing tip with a syringe body between two syringes of the syringe body in the dental mixer illustrated in FIG. 1.

DETAILED DESCRIPTION OF PREFERRED EMBODIMENT

Figure 1:
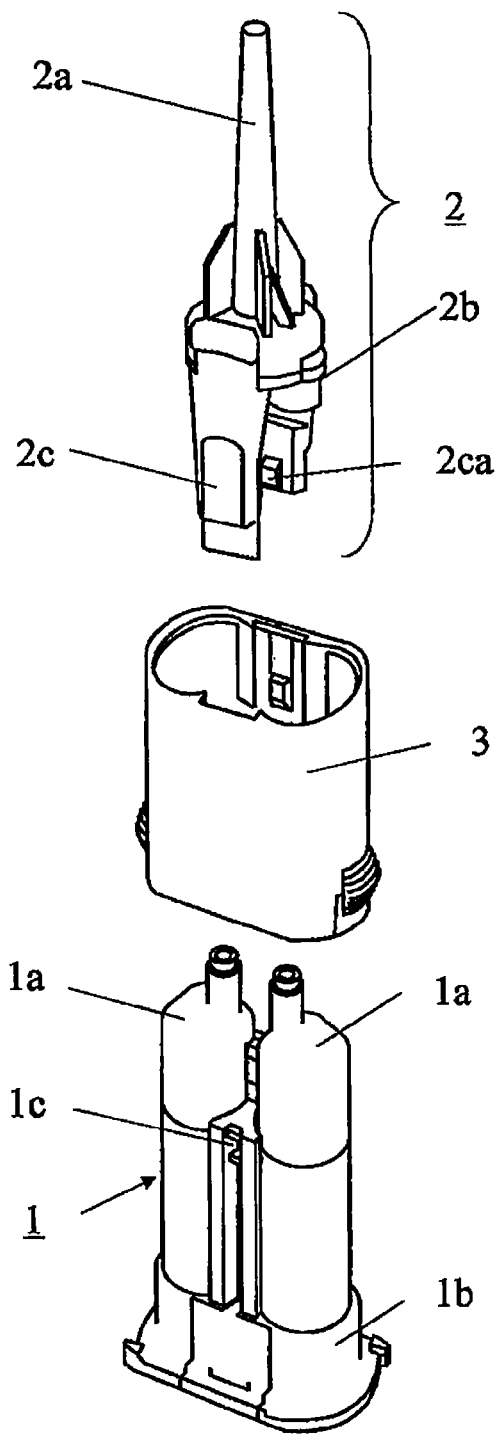
FIG. 1 is a perspective view illustrating one example of a dental mixer according to the present invention.

A dental mixer according to the present invention will be described in detail below with reference to the drawings.

A syringe body 1 includes two parallel syringes 1a and 1a fixed on a holder 1b.

A mixing tip 2 is for mixing and discharging each dental paste in the syringes 1a and 1a. The mixing tip 2 includes a housing 2a, a paste guiding member 2b, and a pair of plate spring-shaped locking members 2c and 2c. The housing 2a has a mixing element mounted inside thereof. The paste guiding member 2b is provided at an end portion positioned on the side opposite to an outlet of the housing 2a, and is for guiding a dental paste from each inside of the syringes 1a and 1a to the inside of the housing 2a. The pair of plate spring-shaped locking members 2c and 2c is constituted integrally with the paste guiding member 2b or the housing 2a, and the locking members 2c and 2c have pawl portions 2ca and 2ca on the tip-end side thereof. The pawl portions 2ca and 2ca of the locking members 2c and 2c are locked, by elasticity, with a pair of locking grooves 1c and 1c each formed between the two syringes 1a and 1a of the syringe body 1.

A sleeve 3 is slidably and externally fitted to the syringes 1a and 1a. The sleeve 3 has a shape, which covers at least the pawl portions 2ca and 2ca of the locking members 2c and 2c when sliding toward the outlet side of the housing 2a and thereby prevents the locking of the pawl portions 2ca and 2ca by elasticity from canceling.

Such the dental mixer according to the present invention includes, as illustrated in FIG. 1, the syringe body 1 including the two parallel syringes 1a and 1a fixed on the holder 1b, the mixing tip 2 for mixing and discharging the dental paste in each of the syringes 1a and 1a, and the sleeve 3 slidably and externally fitted to the syringes 1a and 1a.

The sleeve 3 is externally fitted to the syringes 1a and 1a (the syringe body 1) in a detachable state. However, if the sleeve 3 is previously, externally fitted to the syringes 1a and 1a (the syringe body 1) in an undetachable state (a fixing state or the like), the syringe body 1 and the sleeve 3 are integrated, so that the dental mixer has an easy constitution in which only the mixing tip 2 is attached and detached. Therefore, handling becomes easy.

Figure 2:
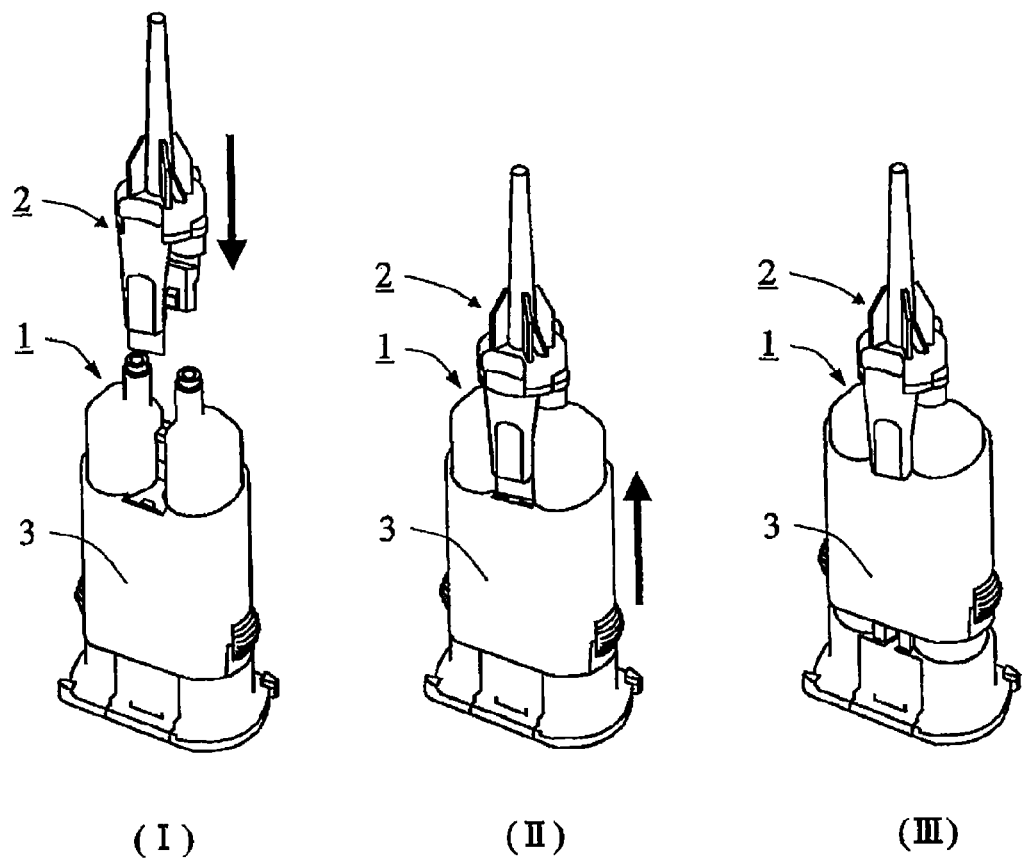
FIG. 2 is a perspective explanation view illustrating a state of locking a mixing tip with a syringe body in the dental mixer illustrated in FIG. 1.

Further, when such the dental mixer according to the present invention is practically used, each of the pawl portions 2ca and 2ca on the tip-end side of the pair of the plate spring-shaped locking members 2c and 2c is previously locked, by elasticity, with the pair of the locking grooves 1c and 1c each formed between the two syringes 1a and 1a of the syringe body 1, as illustrated in FIG. 2 (I) and FIG. 3 (I).

Then, as illustrated in FIG. 2 (II) and FIG. 3 (II), the sleeve 3 slides toward the outlet side of the housing 2a so as to cover at least each of the pawl portions 2ca and 2ca of the locking members 2c and 2c. As a result, the sleeve 3 is in a state that locking of the pawl portions 2ca and 2ca by elasticity is prevented from canceling, as illustrated in FIG. 2 (III) and FIG. 3 (III).

Figure 4:
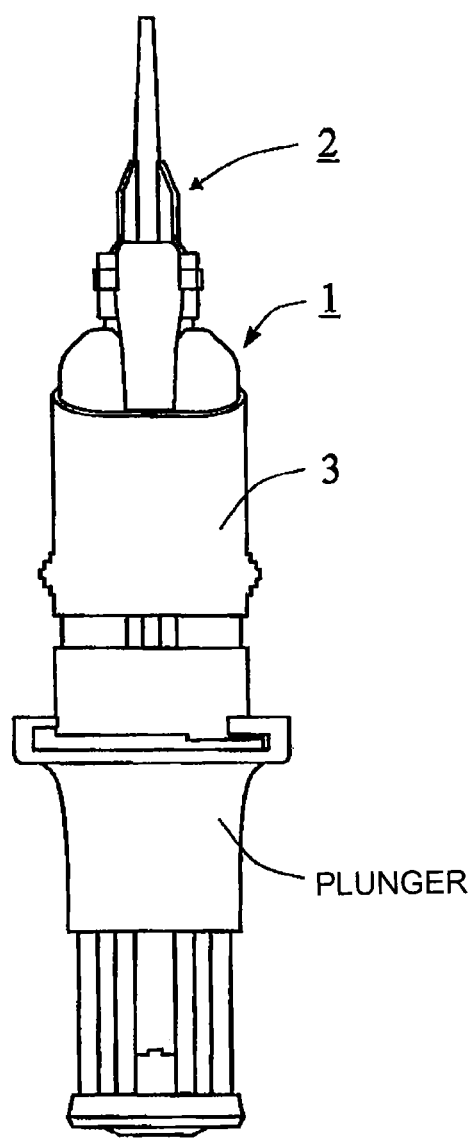
FIG. 4 is a front explanation view illustrating a state of mounting a plunger on the dental mixer illustrated in FIG. 1.

Further, as illustrated in FIG. 4, a plunger is attached to the side opposite to the outlet of the syringe body 1 of the dental mixer according to the present invention. While keeping the state that the sleeve 3 covers at least each of the pawl portions 2ca and 2ca of the locking members 2c and 2c so as not to cancel locking of the pawl portions 2ca and 2ca by elasticity, the plunger is pushed into the syringes 1a and 1a. As a result, the mixed dental paste can be easily discharged from the mixing tip 2.

When the dental mixer is used in the above-mentioned process, mixing and using all dental pastes up in the syringes 1a and 1a are rare, and the dental paste generally remains in the syringes 1a and 1a. If the dental paste remains, the dental paste mixed in the mixing tip 2 is hardened, so that it is difficult to reuse the dental paste later. However, each dental paste remaining in the syringes 1a and 1a are not hardened because the dental paste is not mixed. Therefore, when the dental paste remains in the syringes 1a and 1a, the dental paste can be used later by exchanging the mixing tip 2. As a result, it is very important whether the mixing tip 2 can be exchanged easily or not.

In the dental mixer according to the present invention, since the mixing tip 2 is locked with the syringe body 1 by using the two pawl portions 2ca and 2ca and the sleeve 3 holding the pawl portions 2ca and 2ca, the mixing tip 2 is lightly locked with the syringe body 1 by the pawl portions 2ca and 2ca. Therefore, the mixing tip 2 can be attached and detached easily, and it does not take time and effort to exchange the mixing tip 2, so that handing is very easy.

Namely, when the dental mixer according to the present invention is used as illustrated in FIG. 4 and reused later, the sleeve 3 holding the two pawl portions 2ca and 2ca slides toward the side opposite to the outlet of the syringe body 1. While keeping the state of the sleeve 3, locking of the pawl portions 2ca and 2ca which are locked, by elasticity, with the pair of the locking grooves 1c and 1c of the syringe body 1 is canceled. As a result, the mixing tip 2 can be detached easily. Then, mounting a new mixing tip 2 on the syringe body 1 as mentioned above, all dental pastes remaining in the syringes 1a and 1a can be used without waste.

What is claimed is:

1. A dental mixer comprising:
    a syringe body including two parallel syringes, each of the parallel syringes holding a dental paste therein, and a pair of locking grooves formed between the two parallel syringes, wherein each of the syringes comprise a main body portion and a narrowed neck portion;
    a mixing tip mountable to the syringe body for receiving, mixing and discharging dental paste from the syringes, the mixing tip having an outlet for discharging a mixture of the dental paste received from the two parallel syringes when the mixing tip is mounted to the syringe body;
    a sleeve slidably and externally fitted to the syringe body; and
    a pair of elastic spring plate locking members provided integrally to the mixing tip, each of the elastic spring plate locking members having a pawl portion at a distal end thereof,
    wherein the pawl portions are provided to be elastically locked with the pair of locking grooves when the mixing tip is mounted to the syringe body, and
    wherein the sleeve is positionable on the syringe body to at least partially cover the main body portions of the syringes and is slidable on the syringe body toward the mixing tip, when the mixing tip is mounted to the syringe body, to a position to cover at least the pawl portions of the locking members, thereby to prevent the pawl portions from canceling the locking state with the pair of locking grooves.

2. The dental mixer according to claim 1 wherein the mixing tip further comprises:
    a mixer housing on which the outlet is provided; and
    a paste guiding member provided at an end of the housing opposite to the outlet, for guiding dental paste from inside the two parallel syringes to the inside of the mixer housing.

* * * * *